United States Patent
Gottlund et al.

(10) Patent No.: US 6,312,705 B1
(45) Date of Patent: Nov. 6, 2001

(54) IODOPHOR COMPOSITIONS

(75) Inventors: Kathy L. Gottlund, Kutztown, PA (US); Arthur G. Barnes, New Canaan, CT (US)

(73) Assignee: Puritek, Inc., Short Hills, NJ (US)

(*) Notice: Subject to any disclaimer, the term of this patent is extended or adjusted under 35 U.S.C. 154(b) by 0 days.

(21) Appl. No.: 09/285,763

(22) Filed: Apr. 5, 1999

Related U.S. Application Data

(60) Provisional application No. 60/080,546, filed on Apr. 3, 1998.

(51) Int. Cl.[7] .......................... A01N 25/34; A01N 25/00; A61F 13/00; A61K 9/70; A61L 15/16
(52) U.S. Cl. .......................... 424/404; 424/405; 424/443; 424/445; 424/446; 424/447
(58) Field of Search .................... 424/404, 405, 424/443, 445, 446, 447

(56) References Cited

U.S. PATENT DOCUMENTS 5,128,125 * 7/1992 Barnes .............................. 424/78.08
5,180,585 * 1/1993 Jacobson et al. .................... 424/405

FOREIGN PATENT DOCUMENTS

02295511 * 12/1990 (JP).

* cited by examiner

*Primary Examiner*—Thurman K. Page
*Assistant Examiner*—Todd D Ware
(74) *Attorney, Agent, or Firm*—Walter D. Ames

(57) ABSTRACT

A class of water insoluble iodophors comprising complexes of iodine with various nylons such as nylon-4,6, nylon-6, nylon-6,6 or other polyamides is disclosed. These nylons complexed with iodine can be made in various forms such as powders, pellets, molded objects, granules, films, monofilaments, and either non-woven or woven fabrics. These nylon based iodophors and other water insoluble iodophors herein disclosed can find product applications in the fields of air treatment, water treatment, public hygiene and medicine.

13 Claims, 3 Drawing Sheets

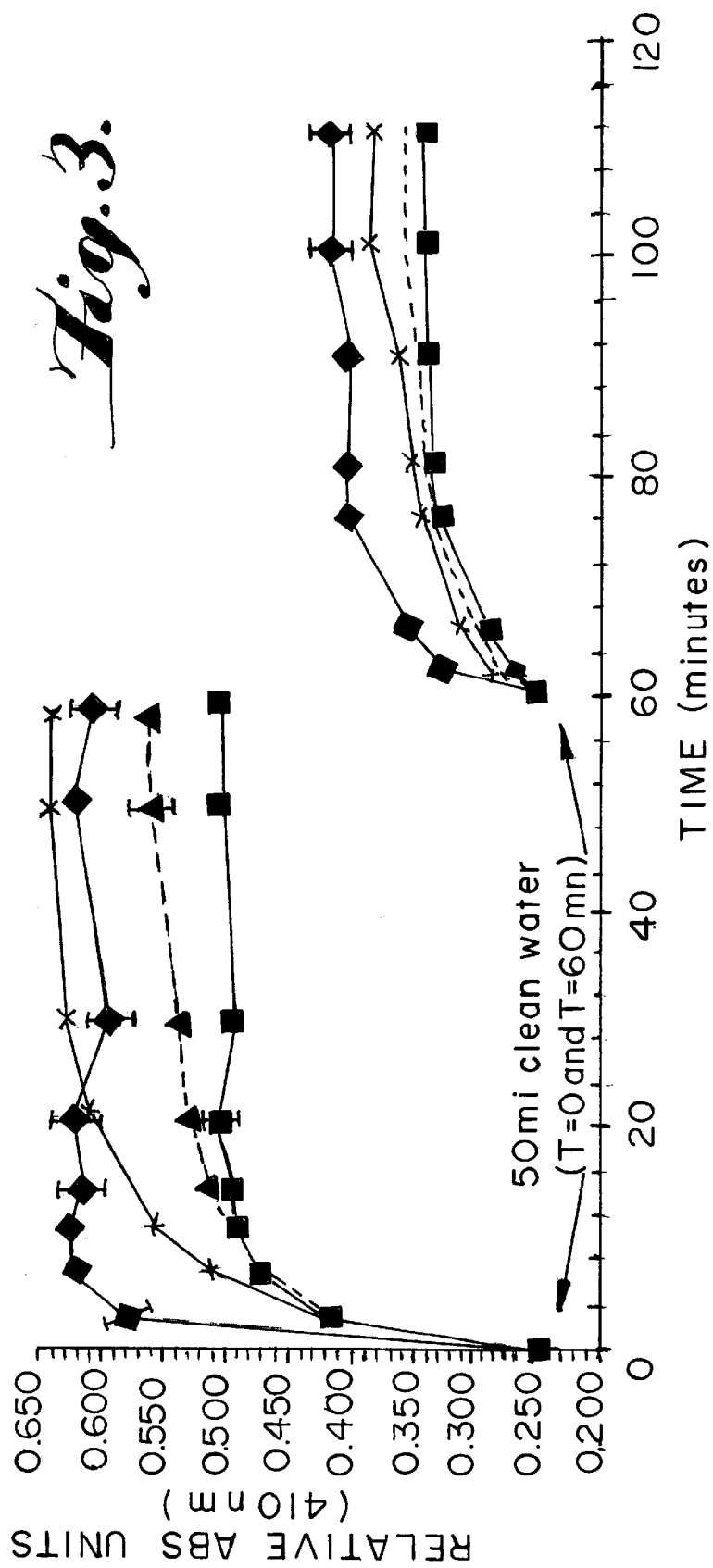

IODOPHOR COMPOSITIONS

This application claims priority based on Provisional Application Ser. No. 60/080,546, filed Apr. 3, 1998.

FIELD OF THE INVENTION

The present invention relates generally to biocidal products designed for the disinfection of water, human or animal skin surfaces, ambient air or other materials. More specifically, it relates to such products which utilize a halogen, preferably iodine, complexed with an insoluble polymer that serves as a carrier for the iodine and releases the iodine to contact with the material to be disinfected.

BACKGROUND OF THE INVENTION

Iodine is one of the oldest and best biocidal agents known, being effective against Gram Positive and Gram Negative bacteria, fungi, spores and viruses. Such knowledge of the disinfecting properties of iodine has given rise to a variety of uses whereby iodine, per se, or as complexed with other materials, is used for those properties. When complexed a sustained release reservoir of iodine is provided.

While the biocidal properties of iodine, a non-metallic, essential element, have been known since the early nineteenth century, iodine does present known difficulties in its use. Despite the fact that iodine reacts with both living and dead microorganisms, it does possess properties that are unsuitable for practical application. Thus, iodine has an unpleasant odor and in contact with the skin stains the skin with an intensive yellow-brown color. When used in laundry in the presence of starch, it causes blue stains and will combine with iron and other metals. Because its solutions are not stable, it irritates animal tissue and is a poison. When brought into direct contact with open wounds, iodine toxicity may occur. Thus, the use of iodine directly for its decontaminating characteristic has been relegated to unusual circumstances and has given rise to compositions known as iodophors.

An iodophor may be defined as a complex of iodine in ionic or molecular form or both with a carrier that serves to increase the solubility of iodine in water and also provides a reservoir of iodine for a controlled and sustained release over time. There are two categories of iodophors, water soluble and water insoluble. An example of a water soluble iodophor is the polyvinylpyrrolidone-iodine complex widely used as a germicidal solution. An example of a water insoluble iodophor is polyvinylalcohol sponge complexed with iodine which can be used to wipe down and disinfect hard surfaces.

In the case of water soluble iodophors one obtains a reduction in the concentration of free available iodine in water as a result of the formation of micellar aggregates with the simultaneous reduction in the disadvantages of iodine per se, i.e., its unpleasant odor, irritation and staining of tissue, and corrosion of metal surfaces. An important factor in creating an iodophor is that one wishes to keep the concentration of free iodine in the solution as low as possible; to be effective.

With respect to specific water-insoluble iodophors and those formed with neutral polymers, it is disclosed in U.S. Pat. No. 5 4,888,118 to Barnes et al. that nylon-4 complexed with iodine may be used for the decontamination of water. In that patent it is disclosed that the use of polypyrrolidone, also known as nylon-4, readily complexes with iodine. Thus, Barnes et al. disclose a water purification process and apparatus whereby the water is first subjected to contact either with iodine or a nylon-4 iodine complex. Sufficient time is allowed for the iodine to destroy microbial organisms present. Then, in another treatment area, the water that has been subjected to iodine treatment is contacted with nylon-4 in a form which provides maximum surface area, and free iodine in the water complexes with the nylon-4 thereby to remove such free iodine and result in water that is potable and decontaminated, despite its prior treatment with iodine.

While the complexing of nylon-4 with iodine is thus known, to the best of our knowledge it is not known whether nylon-4 exhibits properties which, in the Barnes et al. or another setting, will be the most efficacious polymer in providing iodine or iodine-based germicides. In the particular use to which Barnes et al. have put nylon-4, i.e., water purification and subsequent removal of iodine from the water, nylon-4 is certainly of sufficient complexing power as to provide an efficacious iodophor. However, when an iodophor is to be used in order to apply a dressing to a wound, such that the release of an iodine compound or ion for its germicidal properties over a long period of time is desirable, it is now been found that nylon-4 is most certainly not the most effective polymer for forming such an iodophor.

Indeed, quite surprisingly, it is now been found that nylon-4,6 is a superior polymer for forming an iodophor based on the two properties that are most desirable in such a dressing, or allied use. Thus, nylon-4,6 provides for the slow, measured release of iodine compositions from the iodophor into the area to be cleansed. Unexpectedly, nylon-4,6 has been found superior to nylon-6 and nylon-6,6 in this regard, although those polymers as well have been found to be superior to nylon-4 in forming an iodophor with a slow, sustained release of the iodine compounds that have germicidal activity. Further, other natural and synthetic fibers, i.e., wool, a protein fiber, nylon, and other polyamides, may possess advantageous properties when used as iodophors.

SUMMARY OF THE INVENTION

According to the present invention, nylon-6, nylon-6,6 and nylon-4,6 have been found to be useful iodophors and to have properties that make them superior to nylon-4 in such use. More specifically, nylon-4,6, has been found to be the most effective of the various forms of nylon for use as an iodophor. Wool, a polymide rayon, a cellulosic fiber and several other different nylons and other polyamide fibers, but not polyesters have also been determined to be useful iodophors.

BRIEF DESCRIPTION OF DRAWINGS

In the drawings,

FIG. 3 is a graph showing the rate of release of iodine by nylon fibers, plotting time of exposure of the nylon/iodine complexes to water against iodine released into solution.

DETAILED DESCRIPTION OF THE INVENTION

Figure 1:
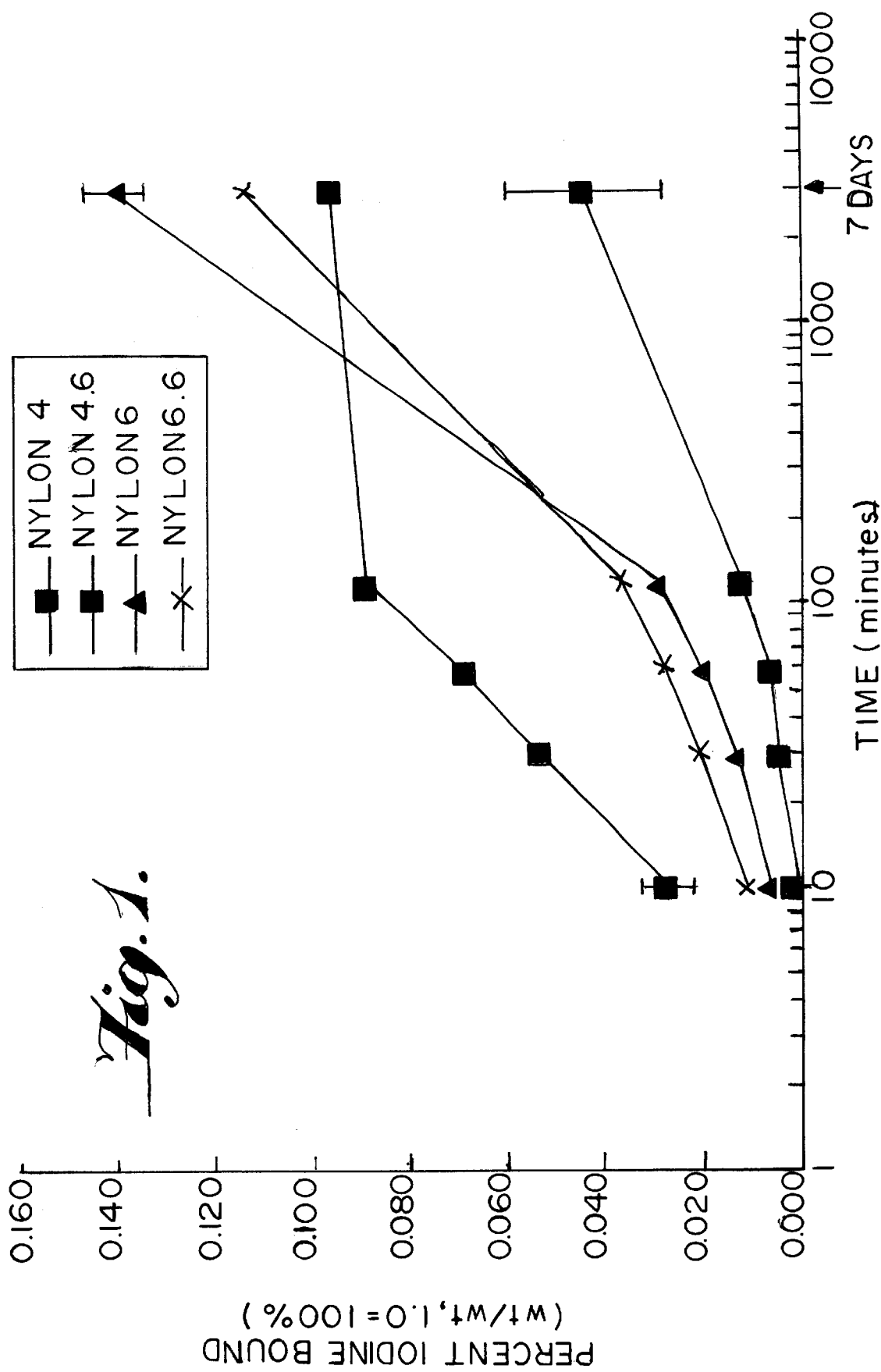
FIG. 1 is a graph showing the rate of take-up of iodine by nylon pellets, plotting time of immersion in the iodine solution against the percent of iodine bound to the nylon.

Prior to detailing the experimentation by which the properties of various nylons when complexed with iodine were evaluated, it is proper to explain the properties that were sought in such an iodophor complex so that the fiber complex would be recognized as suitable for different germicidal uses, for example, as a surgical dressing. What is deemed desirable is a fiber that has the property of "high absorbance capacity, slow release rate" for iodine. In other words, what was sought was a carrier that would slowly take up sufficient amounts of iodine in solution. After the iodine is complexed with the carrier, the property deemed most advantageous was the slow, steady release of small amounts of available iodine in any of its forms. Thus, the composition deemed most desirable is one where the iodophor complex permits a slow release of the iodine in any of its forms from the complex.

With particular regard to the slow release property sought, nylon-4 possesses properties that have been deemed undesirable, that is, it has "high absorption capacity, but quick release rate" for iodine. Nylon-4 rapidly binds to iodine and thereby complexes with large quantities of iodine. However, it also releases large amounts of iodine rapidly, which makes it undesirable for use as a surgical dressing or such other uses where the iodophor is to be used for its germicidal properties over at least a moderate period of time. In the Barnes et al. patent, where nylon-4 was used to acquire iodine after water had been treated with that element, the nylon-4 was certainly a satisfactory composition to use, since it does have high absorption capacity and absorption rate for iodine and therefore was effective in removing iodine from an aqueous solution.

However, even with its high affinity for iodine, nylon-4 will rapidly release its iodine content and therefore will provide an overabundance of iodine to the germicidal site over a short period of time, after which the iodophor utilizing nylon-4 will have substantially exhausted its iodine supply. Nylon-6 and 6,6, and to a greater extent, nylon-4,6 will not complex as rapidly with iodine as nylon-4. However, they will release their complexed iodine over a far longer period of time and, particularly with nylon-4,6, will do so in a steady manner such as to make the use of those nylons for sustained germicidal properties far and unexpectedly different to that of nylon-4.

Experiments were conducted to determine the differences or relative rates in the ability of nylon-4, nylon-4,6, nylon-6, and nylon-6,6 to capture or sequester iodine in the form of tri-iodide and to hold the iodine captive. Pellets of nylon-4, nylon-6, nylon-4,6, and nylon-6,6 were obtained from various sources and washed three times in hot, soapy water. The pellets were then rinsed and dried prior to use. A 0.4 Molar $KI_3$ solution was prepared. Individual glass bottles, sometimes known as anaerobic bottles, were utilized. Five ml. of the $KI_3$ solution was added to each of the 48 bottles, and then preweighed, equal samples of nylon pellets were added to the individual bottles. To 12 of the vials, 1 gram of nylon-4 pellets were added; to another 12, 1 gram of nylon-6 pellets were added; to another 12, 1 gram of nylon-6,6 pellets were added, and to the last 12 bottles, 1 gram of nylon-4,6 pellets were added. At appropriate times, the pellets were collected, washed for three seconds with cold tap water, and placed in weigh boats to dry. The weigh boats were dried for 24 hours at room temperature and weighed to determine the percent of iodine bound.

The results of the iodine uptake abilities of the various nylon-4, nylon-4,6, nylon-6, and nylon-6,6 pellets are shown in FIG. 1. As will be apparent from the graph in FIG. 1, 3 samples of each of the nylon pellets, i.e., 3 bottles of each type of nylon were withdrawn from immersion in the $KI_3$ and 7 days solution after 10 minutes, 30 minutes, 60 minutes, and 120 minutes, respectively. Thereafter, the measurements for samples in triplicate for each specific nylon at each time point were averaged, together with the standard deviation (SD) inherent in the calculations.

The results of this experiment show that the nylon-4 pellets took up more iodine within two hours then either the nylon-4,6, nylon-6, or nylon 6,6 pellets. Indeed, the nylon-4,6 pellets captured the least amount of iodine throughout.

The conclusion to be drawn from these experiments is that the nylon-4 pellets take up more iodine than the nylon-4,6, nylon-6 or nylon-6,6 pellets. Unexpectedly, the nylon-4,6 pellets take up the least amount of iodine, and the nylon-6 and nylon-6,6 pellets capture substantially the same percent of iodine, intermediate to that of nylon-4 and nylon-4,6.

The results of these experiments show that nylon-4,6 pellets are the least effective in capturing iodine. The rate of pick up was the slowest, and levels approaching saturation were approximately 46%, 31%, and 39% of those obtained by the use of nylon-4, nylon-6 and nylon-6,6 pellets, respectively. The ability of nylon-4 pellets to take up iodine is rapid when reached in apparent saturation level after approximately 120 minutes. Nylon-6 and nylon-6,6 appear to be able to take up more of total iodine than nylon-4 and nylon-4,6. This was also unexpected.

Figure 2:
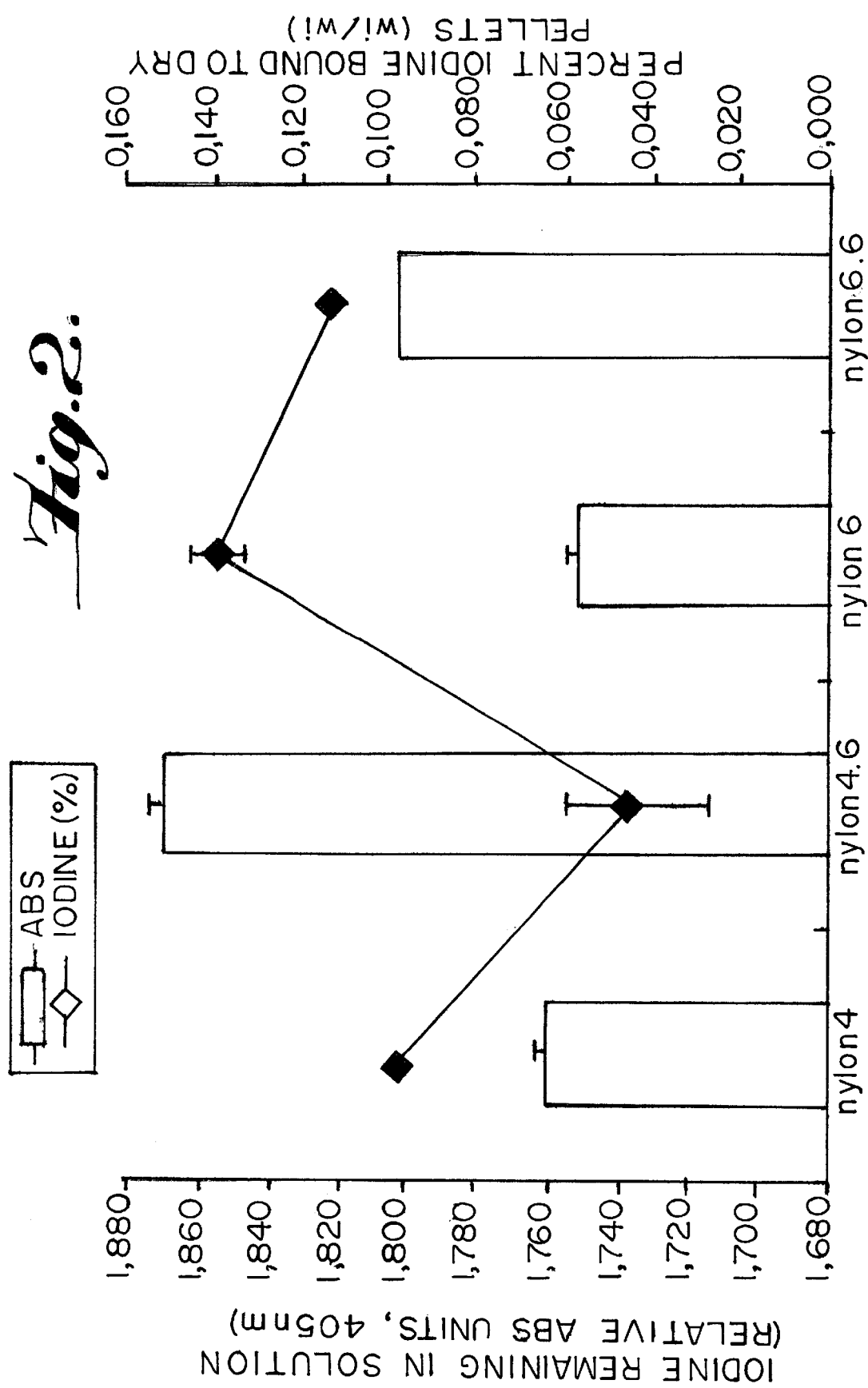
FIG. 2 is a bar graph showing the percent of iodine bound to nylon pellets and residual iodine remaining in solution after seven days exposure to an iodine solution.

As an auxiliary experiment, fresh nylon pellets obtained as previously described were exposed to a $KI_3$ solution for seven days, and the percent of iodine bound to the pellets was calculated as previously described. Further, the relative absorbance units (ABS) of iodine remaining in solution were analyzed using a 96-well ELISA reader. Those results were plotted in accompanying FIG. 2. The ABS values shown are the mean±SD samples analyzed in triplicate. The bar graph shows that a far greater amount of iodine is left in solution by nylon- 4,6 than the other nylons, confirming the inverse relationship of iodine bound vs. iodine in solution.

In order to confirm the examples previously carried out with regard to the tri-iodide form of iodine, the different nylons, all in pellet form, were subjected to tri-iodide exposure to measure how much iodine each would absorb. One-half gram pellets of each nylon were weighted out and each placed into a small glass bottle. Each bottle had 1.0 ml of a stock tri-iodide solution pipetted over the pellets in each bottle. The concentration of iodine was 15% elemental iodine by weight of the total weight of the iodine-KI-water solution, so 100 grams of the stock solution would contain 15 grams of elemental iodine. The total time each of the pellets was exposed to this solution before titration was noted. The procedure of titration was in each case to remove 0.025 ml of the solution over the pellets with a micro-pipette and dissolve it in 40 ml cold tap water in a beaker, then titrate it with a stock solution of sodium thiosulfate from a burette. The stock solution itself used as a control took 3.3 ml of thiosulfate titrant to reach an end point. Therefore, any iodine in the stock solution removed by the nylon pellets would reduce the iodine concentration in the solution over the pellets and less volume of titrant would be required to reach an end point. The volume in mls to reach the end point of a sample divided by 3.5 ml volume of the control times 100 gives the percent iodine remaining in solution.

The titration results are set forth in the following

TABLE 1

| Nylon Type | Time of Exposure | % Remaining Iodine |
| --- | --- | --- |
| nylon-4 | 1 hour | 17% |
| nylon-4,6 | .75 hour | 78.8% |
| nylon-4,6 | 1.2 hour | 75.6% |

TABLE 1-continued

| Nylon Type | Time of Exposure | % Remaining Iodine |
|---|---|---|
| nylon-4,6 | 2.5 hour | 60.6% |
| nylon-6 | 20 minutes | 55.8% |
| nylon-6 | 1 hour | 44.0% |
| nylon-6 | 1.2 hour | 42.0% |
| nylon-11 | 1.0 hour | could not measure* |
| nylon-6,12 | 1.2 hours | could not measure* |

*the volume of titrant in this case to the nearest 1/10 ml was the same as the control which took 3.3 ml to end point. The pellets when rinsed with water were visibly colored with iodine, but there was too little absorbed from solution to measure a drop in the iodine concentration by this method.

This experiment confirmed the observation that nylon-4,6 takes up considerably less iodine than nylon-4 over a given period of time, whether from a solution of elemental iodine or a $KI_3$ solution.

Experiments were then conducted to determine the rate of release of tri-iodide form of iodine from nylon-4, nylon-4,6, nylon-6 and nylon-6,6 in the form of fibers that had been prepared by immersion in $KI_3$ solutions in accordance with the procedures set forth hereinbefore. Samples were first washed thoroughly with soap and water, then dried and weighed. Two-gram samples of each fiber were then exposed to 40 mls of a 0.4M solution of $KI_3$ for a period of 20 hours. After the 20-hour immersion, the samples were rinsed for 10 seconds with cold tap water and dried for iodine determination. These samples were then used to determine release rates for the various nylons as described hereinafter. It is important to note that after 2 hours of immersion total amount of iodine bound to stock samples was:

N4=11%

N4,6=30%

N6=31%

N6,6=25%

One 0.5 gram sample of each nylon fiber was immersed in 50 mls water at room temperature. After 3 minutes, 7 minutes, 11 minutes, 15 minutes, 21 minutes, 30 minutes, 50 minutes, and 60 minutes, two 200 µl samples were taken and the amount of iodine released in the solution was determined by relative absorbance. After 60 minutes it appeared that no more iodine would be released for all four types of nylon. Therefore, a complete 50 ml water change was performed at 60 minutes. Collection of two 200 µl samples was resumed at 61, 66, 76, 81, 91, 101 and 111 minutes to confirm differences in release of iodine by different nylons. Then the average of the two ABS values±standard deviation were calculated and plotted on a graph, which has been included as FIG. 3.

In FIG. 3 there are two parts to the graph, the first showing a plot to indicate the amount of iodine released from 0 to 60 minutes, and then the second to show the amount of iodine lost after a complete 50 ml water change. The symbols shown in the key in the upper right hand corner of FIG. 3 specify the various types of nylon to which the lines pertain. The lines above and below the symbols are intended to show the standard deviations.

The experiments graphed in FIG. 3 show a result that was found to be surprising. Nylon-4, which was quick to take up iodine as shown in FIG. 1, was also quick to release it. This is considered an undesirable property, because it means that the nylon-4, when used in a wound dressing, for example, would tend to flood the wound with iodine and thereby quite probably cause discomfort to the person or animal to which the dressing had been applied. On the contrary, nylon-4,6 which was expected to lie between nylon-4 and nylon-6 in its absorption rate and release rate of the tri-iodide form of iodine, was the slowest to capture or release iodine. The nylon-4,6 had a slow steady release of iodine and therefore is considered the most reliable and preferred nylon fiber or pellet that could be utilized to apply iodine as a biocidal dressing where continued germicidal action is required over a period of time. While still more useful than the nylon-4 fibers, fibers made of nylon-6 and nylon-6,6 fall between nylon-4 and nylon-4,6 in utility. They have a definite place in their use as biocidal dressings; yet their superiority to nylon-4 in such use is not of the same magnitude as the utility of nylon-4,6.

Other experiments were conducted comparing nylon-6,10 to nylon-11, nylon-6,12, nylon-6 and nylon-4, with respect to their take-up of iodine from a solution of elemental iodine in methanol.

A stock solution of iodine in methanol for this experiment was made by dissolving 1 gram of iodine in 25 ml anhydrous methanol. To this methanol-iodine solution was added less than a gram of nylon-6,10 pellets. After 5 minutes of contact a few of the pellets were removed and rinsed. They were very dark brown with iodine but clear. The nylon-6,10 pellets initially are transparent and so are the nylon-6,12 pellets, but the nylon-11 pellets are translucent. After 1 hour the remaining nylon-6,10 pellets became tacky and they stuck together. It was found that nylon-6,10, when exposed to this concentration of iodine in methanol at room temperature, is the only nylon that becomes sticky; nylons 4;11;6,12;4,6 and 6 do not. Nylon-6,10 is unique in this respect.

Nylon-6,10 pellets were exposed to a 10% iodine by weight in water-KI solution and the aqueous tri-iodide solution made the pellets tacky in 1 hour. In 5 minutes the pellets were not yet sticky and had become amber in color after rinsing with water. This shows that nylon-6,10 picks up tri-iodide from this concentration of tri-iodide in water more slowly than iodine in methanol, as in that case the pellets were dark brown in 5 minutes. None of the other nylons tested become sticky when exposed to this concentration of tri-iodide in water at room temperature.

From these experiments the following qualitative observations were determined.

1) Nylon-6,10 absorbs iodine from methanol/iodine solution faster than nylon-6,12.
2) Nylon-6,10 absorbs iodine from a tri-iodide water solution faster than does nylon-6,12.
3) Nylon-6,10 absorbs iodine from a 1 gm iodine in 25 ml methanol solution faster than from a 10% by weight of iodine in a $KI_3$-water solution. Perhaps molecular iodine can diffuse into the nylon-6,10 polymer matrix faster than the tri-iodide ion.
4) Nylon-6,10 from a methanol/iodine solution or from aqueous tri-iodide will retain its iodine in boiling water longer than nylon-6,12 made from the corresponding solution.

As an auxiliary quantitative experiment to the above qualitative experiment the following experiment was run:

A quarter of a gram of each nylon type in the pellet form was weighted out and placed in separate small bottles. Each bottle had 1 ml of a stock 1 gm iodine in 25 ml methanol solution pipetted over the pellets. A 0.025 ml aliquot of the methanol/iodine solution covering the pellet from each bottle was removed and titrated by dissolving in 40 ml of water to which 4 ml of a stock KI-water solution had been added to make the iodine from the methanol/iodine completely soluble in the 40 ml water so it could completely react with the thiosulfate titrant. A control from the methanol/iodine solution was run and found to require an average of 1.5 ml titrant to neutralize. The nylon samples were then tested and the results were:

TABLE 2

| Nylon-6 | required 1.5 ml |
| Nylon-4 | required 1.3 ml |
| Nylon-6,4 | required 1.4 ml |
| Nylon-11 | required 1.4 ml |
| Nylon-6,12 | required 1.5 ml |
| Nylon-6,10 | required 1.0 ml |

The exposure time was 1 hour in each case.

It can be seen that only nylon-6,10 absorbed a significant quantity of iodine from the methanol under these conditions. This shows completely different behavior of these nylons when exposed to $KI_3$ in water VS $I_2$ in methanol.

Other materials were also tested to determine their utility as iodophors that would have a slow release of iodine to a surface to be maintained free of bacteria. Those materials tested were wool, rayon, and polyester greige fibers. The basic results of tests with these materials were that wool absorbs iodine more slowly than nylon-4, at least partially due to its property of resisting wetting. From a visual appearance, nylon-4 absorbed iodine rapidly from a $KI_3$ solution and became black in color. Wool became almost black in color but a lighter shade than nylon-4. Rayon also rapidly absorbed iodine, and its color was almost fully black, not as dark as nylon-4 but darker than wool. Polyester in the form of yarn did not absorb iodine. Polyester fibers remained white throughout the 20 minutes during which it was exposed to iodine.

In a determination of release properties, nylon-4 rapidly released iodine, eventually loosing all of its iodine in approximately 15 minutes of continuous cold water rinsing. Rayon rapidly turned blue during rinsing, due to the presence of cellulose or starch-like structures in its fiber. After about 10 minutes the blue color of rayon faded to lighter shades, and eventually returned to the original white color of the fiber. On the other hand, wool released iodine more slowly than rayon or nylon-4, changing to a dark auburn color and finally to a light auburn color after 20 minutes of rinsing. After the same period of time the nylon-4 sample was almost completely free of iodine. From the results of these tests, the characteristics of slow uptake and slow release of iodine by wool are the most similar to those properties of nylon-4,6, and wool may be considered for specialty products where, for some reason, nylon-4,6 is not appropriate for use. Of the other materials tested, polyester is completely inappropriate for use as a dressing to supply iodine to a surface to be maintained germ-free. Rayon is almost as appropriate as nylon-4, but less appropriate than wool.

While the present application has been primarily concerned with the use of an iodophor to slowly release iodine to a surface to be rendered germ-free, another use of nylon and other fibers would be to bind radioactive isotopes of iodine. In boiling water reactors most of the radioactive iodine is found in the form of the iodide. Volatile species also include $I_2$ and organic iodides. Radioactive iodines are produced from the fission of uranium and plutonium and may enter the human food chain and accumulate in the thyroid gland. Thus, there is a strong potential for the use of nylon to absorb and bind radioactive iodine from waste waters in nuclear power plants, and to hold those iodines in conjunction with the fibers or pellets until those nylon forms have captured the full amount of radioactive iodines that they are capable of holding. In this manner the slow release properties of nylon-4,6 and wool could also be advantageous when compared with the rapid capture, rapid release characteristics of nylon-4.

While our invention as disclosed herein has only been discussed with respect to certain synthetic and natural fibers, as well as pellets of synthetic polymers, it will be obvious to those of skill in the art that certain other fibers and pellets or powders with properties closely aligned to those disclosed may also be of similar, superior effectiveness in the capture and release of tri-iodide ion or iodine in other forms for various uses. It is, therefore, desired that all such applications of and fibers and pellets and film as would be apparent to those of skill in the art from reading the above disclosure be included within the scope of our invention, which is to encompass not only the specific materials disclosed, but all equivalents thereof.

What is claimed is:

1. An iodophor complex formed from iodine and nylon, in which said nylon is nylon-4,6.

2. An iodophor complex as claimed in claim 1, in which said complex is formed by immersing said nylon in an I solution for a period of time sufficient to form a substantial percent of said complex.

3. An iodophor complex as claimed in claim 1, in which said complex is formed by immersing said nylon in a solution of elemental iodine for a period of time sufficient to form a substantial percent of said complex.

4. An iodophor complex as claimed in claim 1, in which said nylon is in the form of a fabric.

5. An iodophor complex as claimed in claim 1, in which said nylon is in the form of pellets or powder.

6. An iodophor complex as claimed in claim 1, in which said nylon is in the form of a suture or monofilament.

7. A biocidal dressing for a wound, comprising fibers of nylon-4,6 that have been complexed with iodine in the form of an $I_2$ solution, elemental iodine, or combinations of an $I_2$ solution and elemental iodine for a period of time sufficient to form a substantial percent of said complex, said dressing, when subjected to an aqueous source, having an improved, slow release of iodine such as to mitigate the discomfort caused by said iodine to said wound.

8. A biocidal dressing as claimed in claim 7, in which said nylon has been complexed with iodine in the form of a solution of potassium tri-iodide.

9. A biocidal dressing as claimed in claim 7, in which said nylon has been complexed with iodine in the form of elemental iodine.

10. A biocidal dressing as claimed in claim 7, in which said nylon has been complexed by immersion in a mixture of potassium tri-iodide and elemental iodine dissolved in an organic solvent.

11. An antimicrobial product comprising an iodophor complex in the form of a fabric as claimed in claim 4, said product being selected from the group consisting of water decontamination devices, air decontamination devices, biocidal face masks, and biocidal socks.

12. An antimicrobial product comprising an iodophor complex in the form of a pellet as claimed in claim 5, said product being selected from the group consisting of sutures, door knobs, keyboard keys and telephone hand sets.

13. An antimicrobial product comprising an iodophor complex as claimed in claim 5, said product consisting of a hand decontamination wash.

* * * * *